United States Patent [19]

Berg

[11] Patent Number: 5,738,764
[45] Date of Patent: Apr. 14, 1998

[54] SEPARATION OF T-AMYL ALCOHOL FROM 2-METHYL-1- PROPANOL BY AZEOTROPIC DISTILLATION

[76] Inventor: Lloyd Berg, 1314 S. 3rd Ave., Bozeman, Mont. 59715

[21] Appl. No.: 827,916

[22] Filed: Apr. 8, 1997

[51] Int. Cl.$^6$ .............................. B01D 3/36; C07C 29/84
[52] U.S. Cl. .................. 203/57; 203/59; 203/62; 203/63; 568/913
[58] Field of Search ..................... 203/62, 63, 57, 203/59; 568/913

[56] References Cited

U.S. PATENT DOCUMENTS

| | | | |
|---|---|---|---|
| 4,416,734 | 11/1983 | Jacobs | 203/18 |
| 4,693,787 | 9/1987 | Berg et al. | 203/57 |
| 4,693,788 | 9/1987 | Berg et al. | 568/913 |
| 4,756,803 | 7/1988 | Berg et al. | 568/913 |
| 4,935,103 | 6/1990 | Berg et al. | 203/57 |
| 5,338,410 | 8/1994 | Berg | 203/63 |
| 5,645,695 | 7/1997 | Berg | 203/57 |
| 5,658,435 | 8/1997 | Berg | 203/57 |

FOREIGN PATENT DOCUMENTS 0047204  3/1982  European Pat. Off. ............ 203/57

*Primary Examiner*—Virginia Manoharan

[57] ABSTRACT

T-Amyl alcohol is difficult to separate from 2-methyl-1-propanol by conventional distillation or rectification because of the proximity of their boiling points. T-Amyl alcohol can be easily separated from 2-methyl-1-propanol by azeotropic distillation. Effective agents are triethyl amine, ethyl ether and acetone.

1 Claim, No Drawings

SEPARATION OF T-AMYL ALCOHOL FROM 2-METHYL-1- PROPANOL BY AZEOTROPIC DISTILLATION

FIELD OF THE INVENTION

This invention relates to a method for separating t-amyl alcohol from 2-methyl-1-propanol using certain organic organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or more of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, | Relative Volatility | | | | | | | |
|---|---|---|---|---|---|---|---|---|
| Both Products | 1.02 | 1.1 | 1.2 | 1.3 | 1.4 | 1.5 | 2.0 | 3.0 |
| (Mole Fraction) | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 23 | 14 | 9 |
| 0.990 | 463 | 95 | 49 | 34 | 26 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

T-Amyl alcohol and 2-methyl-1-propanol boil six degrees apart and have a relative volatility of 1.08 which makes it impossible to separate by conventional distillation or rectification. Table 2 shows that with an agent giving a relative volatility of 1.4 only 36 actual plates are required to get 99% purity.

TABLE 2

Theoretical and Actual Plates Required vs. Relative volatility for t-Amyl Alcohol from 2-Methyl-1-propanol Separation

| Relative Volatility | Theoretical Plates Required At Total Reflux, 99% Purity | Actual Plates Required, 75% Eff. |
|---|---|---|
| 1.3 | 34 | 46 |
| 1.4 | 25 | 36 |
| 1.45 | 24 | 32 |

OBJECTIVE OF THE INVENTION

The object of this invention is to provide a process or method of azeotropic distillation that will enhance the relative volatility of t-amyl alcohol from 2-methyl-1-propanol in their separation in a rectification column. It is a further object of this invention to identify effective azeotropic distillation agents that are stable and can be recycled.

SUMMARY OF THE INVENTION

The objects of this invention are provided by a process for the separation of t-amyl alcohol from 2-methyl-1-propanol which entails the use of certain organic compounds when employed as the agent in azeotropic distillation.

TABLE 3

Effective Azeotropic Distillation Agents For Separating t-Amyl Alcohol From 2-Methyl-1-propanol

| Compounds | Relative Volatility |
|---|---|
| None | 1.08 |
| Acetone | 1.3 |
| Ethyl ether | 1.4 |
| Petroleum ether | 1.35 |
| t-Butyl methyl ether | 1.35 |
| Benzyl ether | 1.35 |
| Ethylene glycol dimethyl ether | 1.35 |
| Triethyl amine | 1.45 |

DETAILED DESCRIPTION OF THE INVENTION

I have discovered that certain organic compounds will effectively increase the relative volatility between t-amyl alcohol and 2-methyl-1-propanol during rectification when employed as the agent in extractive distillation. They are acetone, ethyl ether, petroleum ether, t-butyl methyl ether, benzyl ether, triethyl amine and ethylene glycol dimethyl ether.

THE USEFULNESS OF THE INVENTION

The usefulness or utility of this invention can be demonstrated by referring to the data presented in Tables 1, 2 and 3. All of the successful agents show that t-amyl alcohol can be separated from 2-methyl-1-propanol by means of azeotropic distillation and that the ease of separation is considerable.

WORKING EXAMPLE

Example 1

Fifty grams of a t-amyl alcohol and 2-methyl-1-propanol mixture and fifty grams of trimethyl amine as the azeotrope forming agent were charged to a vapor-liquid equilibrium still and refluxed for two hours. The vapor composition was 38.5% t-amyl alcohol, 61.5% 2-methyl-1-propanol; the liquid composition was 30% t-amyl alcohol, 70% 2-methyl-1-propanol. This is a relative volatility of 1.45.

I claim:

1. A method for recovering t-amyl alcohol from a mixture of t-amyl alcohol and 2-methyl-1-propanol which consists essentially of distilling a mixture consisting of t-amyl alcohol and 2-methyl-1-propanol in the presence of an azeotrope forming agent, recovering the t-amyl alcohol and the azeotrope forming agent as overhead product and obtaining the 2-methyl-1-propanol as bottoms product, wherein said azeotrope forming agent consists of one material selected from group consisting of acetone, ethyl ether, petroleum ether, t-butyl methyl ether, benzyl ether, ethylene glycol dimethyl ether and triethyl amine.

* * * * *